United States Patent [19]

Winkley et al.

[11] Patent Number: 4,801,706

[45] Date of Patent: Jan. 31, 1989

[54] N-SUBSTITUTED-HEXAHYDRO-1,2,5-TRIAZEPINES

[75] Inventors: Michael W. Winkley, Malvern; James L. Diebold, Norristown, both of Pa.

[73] Assignee: American Home Products Corporation, New York, N.Y.

[21] Appl. No.: 187,187

[22] Filed: Apr. 28, 1988

[51] Int. Cl.⁴ .................. C07D 255/02; A61K 31/55
[52] U.S. Cl. ........................................ 540/554; 514/183
[58] Field of Search ......................................... 540/544

[56] References Cited

PUBLICATIONS

Szotor et al., Dissert. Pharm. Pharmacol., XXIV, 385–390, (1972): Chem Abst. 77: 152134z, (1972).

Primary Examiner—Robert T. Bond
Attorney, Agent, or Firm—Arthur G. Seifert

[57] ABSTRACT

Disclosed herein are N-substituted-hexahydro-1,2,5-triazepines of formula I, which is

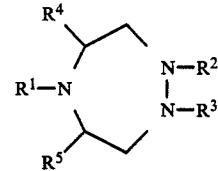

or a pharmaceutically acceptable acid addition salt thereof, wherein $R^4$ and $R^5$ are independently hydrogen or $C_1$–$C_4$ alkyl;
$R^1$ is $(R^6)_2$—CH—$(CH_2)_n$— in which n is 0, 1, 2 or 3 and $R^6$ is p-fluoro, chloro or methoxyphenyl; and
$R^3$ is hydrogen and $R^2$ is benzoyl, 2,6-dimethyl or diethylbenzoyl, 2,6-dichlorobenzoyl, N-methyl, ethyl or propylcarboxamido, N-phenylcarboxamido, N-2,6-dimethyl or diethylphenylcarboxamido, N-2,6-dichlorophenylcarboxamido, N-methyl, ethyl or propylacetamido, N-phenylacetamido, N-2,6-dimethyl or diethylphenylacetamido, or N-2,6-dichlorophenylacetamido or
$R^2$ and $R^3$ are the same and are N-methyl, ethyl or propylcarboxamido, benzoyl, 2,6-dimethyl or diethlbenzoyl, 2,6-dichlorobenzoyl, benzyl, 2,6-dimethyl or diethlbenzoyl, 2,6-dichlorobenzoyl, or a removable amino protective group. Also disclosed are N-substituted-hexahydro-1,2,5-triazepines of formula II in which $R^1$ of formula I is replaced by $R^7$ which is $C_1$–$C_4$ alkyl, and $R^2$ and $R^3$ of formula I are replaced by $R^8$ and $R^9$ which are, respectively, N-2,6-dimethyl, diethyl or dichlorophenylcarboxamido or N-2,6-dimethyl, diethyl or dichlorophenylacetamido and hydrogen. The compounds of the invention have antiarrhythmic properties or are intermediates for the preparation thereof.

23 Claims, No Drawings

N-SUBSTITUTED-HEXAHYDRO-1,2,5-TRIAZEPINES

This invention comprises hexahydro-1,2,5-triazepines of formulas I and II below: formula I

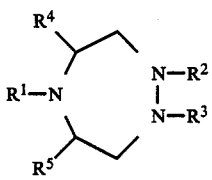

or a pharmaceutically acceptable acid addition salt thereof, wherein $R^4$ and $R^5$ are independently hydrogen or $C_1$–$C_4$ alkyl;

$R^1$ is $(R^6)_2$—CH—$(CH_2)_n$— in which n is 0, 1, 2 or 3 and $R^6$ is p-fluoro, chloro, or methoxyphenyl; and $R^3$ is hydrogen and $R^2$ is benzoyl, 2,6-dimethyl or diethylbenzoyl, 2,6-dichlorobenzoyl, N-methyl, ethyl or propylcarboxamido, N-phenylcarboxamido, N-2,6-dimethyl or diethylphenylcarboxamido, N-2,6-dichlorophenylcarboxamido, N-methyl, ethyl or propylacetamido, N-phenylacetamido, N-2,6-dimethyl or diethylphenylacetamido, or N-2,6-dichlorophenylacetamido; or $R^2$ and $R^3$ are the same and are N-methyl, ethyl or propylcarboxamido, benzoyl, 2,6-dimethyl or diethylbenzoyl, 2,6-dichlorobenzoyl, benzyl, 2,6-dimethyl or diethylbenzyl, 2,6-chlorobenzoyl, or a removable amino protective group: and formula II

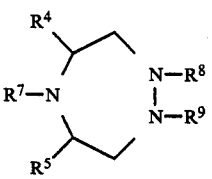

or a pharmaceutically acceptable acid addition salt thereof, wherein $R^4$ and $R^5$ are independently hydrogen or $C_1$–$C_4$ alkyl;

$R^7$ is $C_1$–$C_4$ alkyl; and $R^9$ is hydrogen and $R^8$ is N-2,6-dimethyl, diethyl or dichlorophenylcarboxamido or N-2,6-dimethyl, diethyl or dichlorophenylacetamido; or $R^8$ and $R^9$ are the same and are a removable amino protective group.

The compounds of formulas I and II exhibit pharmacological properties as antiarrhythmic agents or are intermediates for the preparation of such pharmacologically active compounds.

Szotor et al., "Synthesis of hexahydro-1,2,5-triazepine derivatives", Dissert. Pharm. Pharmacol. (Engl.), 1972, XXIV, 4, pp 385–390, (Chem. Abst.: 77 152132, 1972) report the preparation of three hexahydro-1,2,5-triazepines. No particular pharmacological activity was investigated or reported for this group of compounds. The three reported hexahydro-1,2,5-triazepines are: (1) 1,2-bis(1-methylethyl)hexahydro-5-methyl-1H-1,2,5-triazepine, (2) 1,2-bis(1-methyl-methylethyl)hexahydro-5(phenylmethyl)-1H-1,2,5-triazepine, and (3) hexahydro-1,2-dimethyl-5-(phenylmethyl)-1H-1,2,5-triazepine.

DETAILED DESCRIPTION OF THE INVENTION

Preferred compounds of the invention are formula I are those in which $R^4$ and $R^5$ are independently hydrogen or methyl; n is 3; $R^6$ is p-fluorophenyl; and $R^3$ is hydrogen and $R^2$ is N-methylcarboxamido, N-ethylcarboxamido, 2,5-dimethylbenzoyl, N-phenylcarboxamido, N-2,6-dimethylphenylcarboxamido, N-methylacetamido, N-phenylacetamido or N-2,6-dimethylphenylacetamido; or $R^2$ and $R^3$ are the same and are benzoyl, benzyl or N-ethylcarboxamido; or $R^2$ and $R^3$ are the same and are a removable amino protective group selected from a group comprising $C_1$–$C_6$ alkanoyl, halo or dihalo($C_1$–$C_6$)alkanoyl, pyridinoyl, t-butyloxycarbonyl, trichloroacetyl, $C_1$–$C_6$ alkoxycarbonyl and p-methoxybenzyl.

Most preferred compounds of the invention of formula I are those in which $R^4$ and $R^5$ are hydrogen; n is 3; $R^6$ is p-fluorophenyl; and $R^3$ is hydrogen and $R^2$ is N-phenylcarboxamido, N-2,6-dimethylphenylcarboxamido, benzoyl, or N-2,6-dimethylphenylacetamido; or $R^2$ and $R^3$ are the same and are benzoyl or benzyl.

The compounds of formula I in which $R^2$ and $R^3$ are the same and are benzoyl or benzyl are active antihypertensive agents. The benzoyl and benzyl groups also may serve as removable amino protective groups in the synthesis of other compounds of formula I or formula II of the invention.

Preferred compounds of formula II of the invention are those in which $R^4$ and $R^5$ are independently hydrogen or methyl; $R^7$ is methyl or ethyl; and $R^9$ is hydrogen and $R^8$ is N-2,6-dimethyl or diethylphenylcarboxamido. Particularly preferred compounds of the invention of formula II are those in which $R^5$ and $R^5$ are hydrogen; $R^7$ is methyl or ethyl; and $R^9$ is hydrogen and $R^8$ is N-2,6-dimethylphenylcarboxamido.

The preparation of the compounds of formula I of the invention is shown in Scheme I below. In this preparation the 5 position nitrogen is protected by a phenyl group while the 1 and 2 position nitrogens are protected with a benzoyl or a benzyl group.

Scheme I

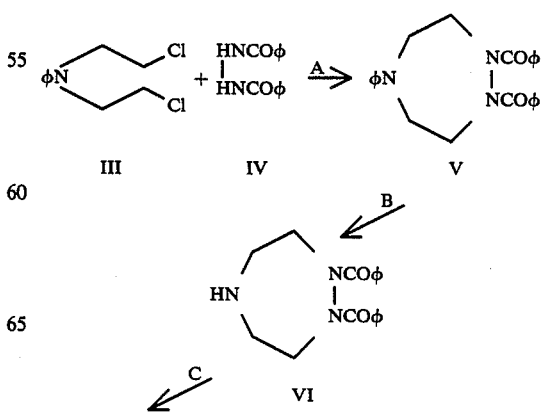

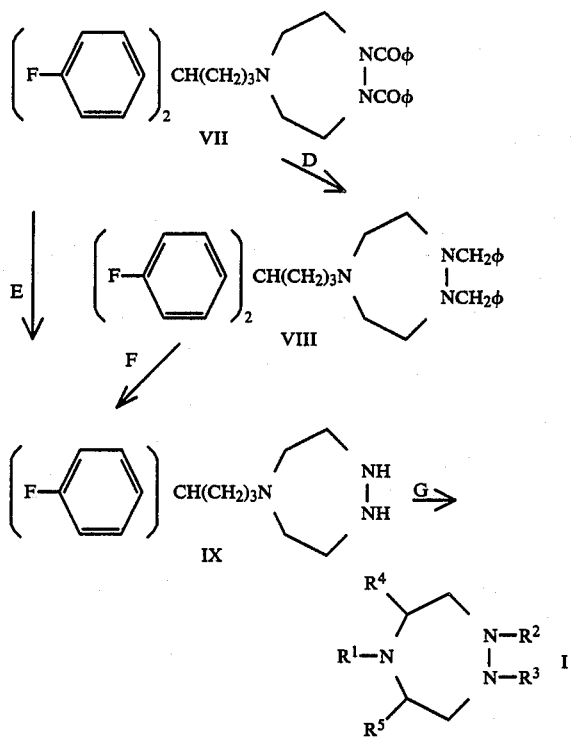

The 1,2,5-triazepine ring system is synthesized by a novel method involving the reaction (A) of a diacylhydrazine (IV) with an appropriate bis(haloethyl)amine (III). N,N'-dibenzoylhydrazine was used in the practice of the invention. Examples of appropriate bis(haloethyl)amines (III) are N,N-bis(chloroethyl)aniline, N-benzyl-N,N-bis(chloroethyl)amine and N,N-bis(chloroethyl)-N-ethylamine. The reaction of step A is carried out in an inert, polar, aprotic solvent, such as N,N-dimethylformamide, dimethylsulfoxide or sulfolane, in the presence of a base, such as potassium t-butoxide or sodium hydride. In the preparation shown in Scheme I, the intermediate V was isolated readily in crystalline form (Example 1).

In step B, the 5-phenyl protective group was removed by hydrogenolysis over palladium in the presence of an acid [R. Kuhn and H. J. Haas, Leibigs Ann., 611, 57 (1958)]. 2 moles of hydrogen were used per mole of the 5-phenyl-1,2,5-triazepine (Example 5). In step C, a 4,4-bis(4-substituted phenyl)alkyl halide is condensed with the 1-nitrogen of the 1,2,5-triazepine (Examples 7 and 8). The halide may be bromine or chlorine or another suitable leaving group may be used, such as a tosyl group, under conditions fostering nucleophilic substitution on a secondary nitrogen. Alternately, a vinyl condensation may be used in step C to condense the $R^1$ group to the deprotected 1,2,5-triazepine (VI). This is illustrated in Example 16 where 4-vinylpyridine is condensed with 1,2-dibenzoyl-1H-1,2,5-triazepine.

In step E or F the 1,2-protected-1,2,5-triazepine VII or VIII is deprotected. In example 11 the 1,2-dibenzoyl protective groups were reduced to benzyl groups with lithium aluminum hydride. In Example 12, the 1,2-dibenzyl protective groups were removed by hydrogenation with palladium. In Example 13, the 1,2-dibenzoyl protective groups were removed by treatment with concentrated hydrochloric acid.

In step G, the various 1 and/or 2 substituents are put in place by condensation with the free amines at this position. In Examples 14–19 one or two moles of the appropriate acid chloride, isocyanate, acetamide or halide are condensed with the 1,2-deprotected-5-substituted-1,2,5-triazepine IX to form the desired product of formula I. The particular reactants used are benzoyl chloride (Ex. 14), ethyl isocyanate (Ex. 15 and 16), phenyl isocyanate (Ex. 17), 2,6-dimethyl phenylisocyanate (Ex. 18) and 2-chloro-N-(2,6-dimethylphenyl)acetamide (Ex. 19).

The compounds of formula II of the invention ($R^7$ is $C_1$–$C_4$ alkyl) may be formed by starting with a N,N-bis(chloroethyl)-N-$C_1$–$C_4$ alkylamine III to react with the appropriate hydrazine IV in step A of Scheme I. Thereafter, the 1,2-aminoprotective groups (eg. benzoyl or benzyl) may be removed (as described above) and the desired $R^8$ moiety added (as described above) as shown in Example 22.

In the case where $R^7$ is methyl, another method of making the corresponding intermediate IX in which the $R^7$ is methyl group is in place and the 1,2-nitrogens are deprotected, is shown in Examples 9, 20 and 21. In Example 9, the reaction 4,4-bis(4-fluorophenyl)butyl bromide with 1,2-dibenzoyl-1H-1,2,5-triazepine hydrochloride in the presence of powdered potassium carbonate produced an intermediate 5-[4,4-bis(4-fluorophenyl)butyl]carboxylic acid ester. Reduction of this ester in Example 20 yielded the desired methyl group in the 5 position and reduced the benzoyl protective moieties to benzyl protective moieties. Catalytic hydrogenation produced the desired hexahydro-5-methyl-1H-1,2,5-triazepine as shown in Example 21.

The compounds of formula I and II of the invention and various intermediate compounds therefore may exist in either the form of a free base or an acid addition salt thereof. Methods of converting the free base to a salt or vice versa are well known in the art. Particular salts may be utilized for isolation and/or characterization of such compounds. For pharmacological and therapeutic use the compounds of formulas I and II of the invention may be used or administered in the free base form or as a physiologically acceptable acid addition salt. For therapeutic use, pharmaceutically acceptable salts are preferred. The preparation and use of such salts is well known. Examples of such acid addition salts are those formed from the following inorganic and organic acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic. The use of such salts in the preparation and isolation of compounds of the invention is illustrated in the examples.

A standard pharmacological procedure used to determine anti-arrhythmic activity in standard experimental animals is as follows:

Rats weighing between 400–500 gms are anesthesized with 35–40 mg/kg sodium pentobarbital intraperitoneally. Rats are close-clipped on the neck and left thorax prior to cannulation of the jugular vein and carotid artery for measurement of arterial blood pressure and injection of drug. A tracheotomy is performed and respiration provided by a Harvard Model 681 respirator at a rate of approximately 55 cycles/min and a volume of 4 cc per cycle. The rat is then placed upon its right side and the heart is exposed by making an incision and separating the ribs. 4-O Silk on taper R-B-1 needle is passed under the left anterior descending coronary artery (LAD) at a location just under the tip of the left atrial appendage. The suture is left to be tied upon occlusion.

The subject rat is allowed to stabilize for 5 to 15 minutes before the administration of drug as a bolus via the cannulated jugular vein. The total drug dose volume is kept constant between 0.20–0.25 ml. Fifteen minutes after dosing, the LAD is occluded by tying the suture. This procedure provokes severe ventricular arrhythmias, terminating in ventricular fibrillation and death in at least about 65 percent of animals given vehicle only. The development and progression of ventricular arrhythmia is monitored for a period of 20 minutes. Lead II ECG and cardiotachometer output are recorded on a Beckman R612 recorder.

Mean arterial pressure (MAP) is monitored throughout the experiment and the following values recorded: (1) MAP prior to drug, (2) maximal change in MAP following drug and before LAD occlusion, and (3) MAP just prior to LAD occlusion. Changes in cardiac electrical activity are determined from the Lead II electrocardiogram. The dysrhythmias are scored as follows: (1) normal sinus rhythm, (2) isolated premature ventricular complexes, (3) nonsustained ventricular tachycardia (repetitive beats of ventricular origin lasting <15 sec.), (4) sustained ventricular tachycardia (repetitive ventricular activity lasting >15 sec.), (5) self-terminating or reversible ventricular fibrillation (VF rev), and (6) irreversible VF (VF irrev. death). The incidence of death in the drug-treated group is then compared to that in the untreated control group (generally >65%). Five animals are included in each drug group.

Arrhythmia scores are calculated for each group of animals for purposes of obtaining more quantitative rankings for anti-arrhythmic efficacy. The equation, $$\sum_{n=1} A \times AS$$

is used, where A=fraction of animals with a certain kind of arrhythmias (e.g., ventricular fibrillation, sustained ventricular tachycardia) and AS is the arbitrary score assigned to that arrhythmia:

| A | AS |
|---|---|
| (a) no arrhythmia | −5 |
| (b) isolated premature beats (PVC's) | +5 |
| (c) non-sustained ventricular tachycardia | +10 |
| (d) sustained ventricular tachycardia | +20 |
| (e) reversible ventricular fibrillation | +40 |
| (f) death | +50 |

Thus, for the purpose of these coronary ligation (C.L.) experiments, a score from −5 (nor arrhythmia) to 50 (death) is assigned to the response of each rat in a test group, based upon the number, type and severity of each response. The sum of the percent of animals at each response level times the point score assigned to that response level equals the score value of the compound being tested. The lower the score, the more active the compound in preventing ventricular dysrhythmia.

References for the above pharmacological procedure are H. Selye et al., Angiology, 11, 398–407 (1960) and J. L. Bergey et al., European Journal of Pharmacology, 81, 205–216 (1982). Scores according to the above procedure for several compounds of the invention are given in Table I below.

TABLE I

| Compound of Example No. | Anti-Arrhythmic Activity | |
|---|---|---|
| | Dose mg/kg | Score |
| 11 | 3 | 14 |
| | 10 | 22 |
| 14 | 10 | 15 |
| 15 | 10 | 30> |
| 17 | 5 | 12 |
| 18 | 1.0 | 29 |
| | 2.5 | 13 |
| | 5.0 | 20 |
| 19 | 10 | 28 |

The two runs of this procedure for the intermediate dibenzoyl compound of Example 8 gave scores of 3 and 32, each at a dose of 3 mg/kg. However, the procedure was not rerun with this compound.

In a standard pharmacological procedure to determine a compound's ability to inhibit $Ca^{2+}$ dependent isometric tension in arterial smooth muscle, the compounds of Examples 15 and 16 showed marked and moderate activity, respectively. This procedure is carried out in a manner similar to that of A. Brockaert et al., European Journal of Pharmacology, 53, 281–288 (1979).

Those compounds of the invention which are described above as antiarrhythmic agents are useful in the treatment of cardiac arrhythmias and conditions characterized by coronary artery occlusion and the resulting myocardial ischemia in mammals, particularly in man. For that purpose, such compounds or their non-toxic, pharmaceutically acceptable salts, may be administered orally or paranterally in suitable dosage forms compatible with the route of administration, whether oral, intraperitoneal, intramuscular, intravenous, intranasal, buccal, etc. The effective dose range determined in the animal test models have been established at from 1 to about 100 milligrams per kilogram host body weight to be administered in single or plural doses as needed to relieve the arrhythmatic dysfunction. The specific dosage regimen for a given subject will depend upon age, pathological state, severity of dysfunction, size of the subject, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavoring or coloring. Parenteral administration with liquid unit dosage forms may be via sterile solutions or suspensions in acqueous or oleagenous medium. Isotonic acqueous vehicle for injection is preferred with or without stabilizer, preservatives and emulsifiers.

The manner and best mode of carrying out the practice of the invention is further illustrated by the following examples.

EXAMPLE 1

1,2-Dibenzoylhexahydro-5-phenyl-1H-1,2,5-triazepine

A mixture of N,N'-dibenzoylhydrazine (140 g) in N,N-dimethylformamide (6.1 L) and benzene (500 ml) was azeotropically dried by the distillation of 700 ml of solvent. Potassium t-butoxide (130.4 g) and benzene (500 ml) were then added and the mechanically stirred mixture was distilled once more to remove 700 ml of solvent. Bis(chloroethyl)aniline (126.9 g) was added and the transfer was completed by the addition of a small volume of dry (4A molecular sieves) N,N-dimethylformamide. The mixture was stirred and heated under reflux with protection from moisture for 5½ hours. The cooled mixture was filtered through celite and the filtrate was evaporated to solid under oil pump vacuum. The solid was mixed with ether, collected on a filter and air dried. The solid was extracted with boiling benzene (3l.) and the extract was filtered through Celite to remove unreacted N,N'-dibenzoylhydrazine. The filtrate was warmed on a steam bath and left to cool to room temperature overnight. A further small quantity of N,N'-dibenzoylhydrazine was removed by filtration through Celite and the resulting solution was evaporated to small volume (under 1.1.). Warming caused crystallization. Addition of ether completed crystallization of the titled compound; wt. 96.0 g (42.7%), mp=190°–192°.

Analysis for: $C_{24}H_{23}N_3O_2$: Calculated: C, 74.78; H, 6.01; N, 10.90. Found: C, 75.20; H, 5.82; N, 10.72.

EXAMPLE 2

Hexahydro-5-phenyl-1H-1,2,5-triazepine

A mixture of 1,2-dibenzoylhexahydro-5 phenyl-1H-1,2,5-triazepine (101.3 g), n-butanol (450 ml), 12N hydrochloric acid (915 ml) and water (915 ml) was mechanically stirred and heated under reflux on a steam bath overnight. Additional 12N hydrochloric acid (400 ml) and water (400 ml) were added and stirring and heating under reflux on a stea bath were continued for three days. n-Butanol (150 ml) was added and stirring and heating under reflux on a steam bath were continued for a further three days. After this time (7 days) the solid had dissolved. The mixture was extracted twice with ether and the aqueous solution was evaporated to smaller volume. Coevaporation with ethanol and concentrated hydrochloric acid caused crystallization of the titled product as the dihydrochloride salt; wt. 57.5 g (66%), mp=211°–218°.

Analysis for: $C_{10}H_{15}N_3 \cdot 2HCl$: Calculated: C, 48.01; H, 6.85; N, 16.80; Cl, 28.34. Found: C, 47.84; H, 7.01; N, 16.62; Cl, 28.04.

EXAMPLE 3

1,2-Dibenzoyl-4-cyclohexylhexahydro-1H-1,2,5-triazepine

A mixture of 1,2-dibenzoyl-5-phenyl-1H-1,2,5-triazepine (20.0 g), dioxane (600 ml), 1N hydrochloric acid (250 ml) and 10% Palladium on carbon (1.0 g) was hydrogenated in a Parr apparatus at 19 p.s.i. pressure for 2 days. The catalyst was filtered and washed with water. After evaporation of the filtrate, the residue was stirred with triethylamine (14 ml) and dichloromethane (150 ml) for ½ hour. Tetrahydrofuran was added and the chilled slurry stirred for 2 hours. The precipitate was removed by filtration and the filtrate was evaporated to a solid. The crude product was chromatographed on a column of silica gel. Elution with ethanol-ethyl acetate-dichloromethane (1:4:5) gave two products (fractions 1 and 2). The earlier eluted material (fraction 1) was recrystallized from ether giving title compound; wt. 0.75 g (3.7%), mp=138°–139°. A fumarate salt (2:1) (mp=200°–201°) was formed in ethanol from this compound.

Analysis for: $C_{24}H_{29}N_3O_2 \cdot \frac{1}{2}(C_4H_4O_4)$: Calculated: C, 69.46; H, 6.95; N, 9.35. Found: C, 69.77; H, 6.97; N, 9.49.

EXAMPLE 4

1,2-Dibenzoylhexahydro-1H-1,2,5-triazepine

Fraction 2 from example 3 was recrystallized from ethyl acetate to give titled product as the free base; wt. 9.3 g (58%), mp=157°–158°.

Analysis for: $C_{18}H_{19}N_3O_2$ Calculated: C, 69.88; H, 6.19; N, 13.58 Found: C, 69.70; H, 6.17; N, 13.73.

A fumarate salt (1:1) of the titled compound was formed in ethanol from this base and was recrystallized from methanol, mp=198°–199°.

Analysis for: $C_{18}H_{19}N_3O_2C_4H_4O_4$ Calculated: C, 62.11; H, 5.45; N, 9.88 Found: C, 62.11; H, 5.75; N, 10.06

EXAMPLE 5

1,2-Dibenzoylhexahydro-1H-1,2,5-triazepine

A mixture of 1,2-dibenzoyl-5-phenyl-1H-1,2,5-triazepine (25.0 g), dioxane (500 ml), N-hydrochloric acid (250 ml) and 10% Palladium on carbon (1.3 g) was hydrogenated in a Parr apparatus at 16 p.s.i. pressure for 19½ hours. The catalyst was removed by filtration and washed with water. The filtrate and washings were evaporated to a solid hydrochloride salt which was dried under oil pump vacuum; wt. 22.4 g. The material was assayed by HPLC and shown to be 91% pure. Material prepared in this way was used directly in further syntheses, e.g., in example 8.

EXAMPLE 6

1,5-Dibenzoylhexahydro-1H-1,2,5-triazepine

A mixture of 1,2-dibenzoyl-1H-1,2,5-triazepine (2.0 g), methanol (100 ml) and acetic acid (10 ml) was stirred and heated at 65° under a nitrogen atmosphere for two days. The residue obtained after evaporation of the solvent, was made alkaline with 10% sodium carbonate solution and extracted with ethyl acetate. The dried ($Na_2SO_4$) solution was evaporated, leaving 2.0 g of a tacky solid. This crude product was chromatographed on a column of silica gel; elution with ethanol-ethyl acetate-dichloromethane (1:4:5) giving one major product, wt. 1.1 g (55%). Recrystallization of this material from aqueous methanol afforded the titled compound as a ¼ hydrate, mp=93°.

Analysis for: $C_{18}H_{19}N_3O_2 \cdot \frac{1}{2}H_2O$: Calculated: C, 68.88; H, 6.26; N, 13.39; $H_2O$, 1.43. Found: C, 69.01; H, 6.31; N, 13.18; $H_2O$, 1.43.

EXAMPLE 7

1,2-Dibenzoyl-5-[4,4-bis(4-fluorophenyl)butyl]-hexahydro-1H-1,2,5-triazepine

A mixture of 4,4-bis(4-fluorophenyl)butyl bromide (2.08 g), 1,2-dibenzoyl-1H-1,2,5-triazepine (2.0 g), powdered anhydrous sodium carbonate (2.71 g) and N,N-dimethylformamide (20 ml, dried over 4A molecular sieves) was stirred at room temperature under a nitrogen atmosphere for three days. The mixture was filtered and the filtrate was evaporated under oil pump vacuum to an oil. The oil was chromatographed on a column of silica gel; elution with ethyl acetate-dichloromethane (2:3) giving a major product. The hydrochloride salt of the titled compound was formed in ether from this material; wt. 2.0 g (52%), mp=216°–218°.

Analysis for: $C_{34}H_{33}F_2N_3O_2.HCl$: Calculated: C, 69.20; H, 5.81; Cl, 6.01; N, 7.12. Found: C, 69.10; H, 5.77; Cl, 6.57; N, 7.27.

EXAMPLE 8

1,2-Dibenzoyl-5-[4,4-bis(4-fluorophenyl)butyl]-hexahydro-1H-1,2,5-triazepine

To a stirred mixture of 1,2-dibenzoylhexahydro-1H-1,2,5-triazepine hydrochloride (13.0 g), powdered anhydrous sodium carbonate (17.8 g) in N,N-dimethylformamide (100 ml, dried over 4A molecular sieves) under a purging nitrogen atmosphere was added 4,4-bis(4-fluorophenyl)butyl bromide (13.66 g) in N,N-dimethylformamide (30 ml) over a period of 40 minutes. The mixture was stirred under a purging nitrogen atmosphere at room temperature for 3 days. The mixture was filtered through sintered glass and the filter pad washed with N,N-dimethylformamide. The filtrate and washings were evaporated at 30° under oil pump vacuum. The residual oil was extracted with ether and the extract was filtered. The solution was slurried with 200 g of silica gel for 20 minutes. The mixture was then filtered through a sintered glass filter. The silica gel was stirred repeatedly with fresh ether (10–15 times) until no more product was removed from the silica gel. The filtrate and washings were evaporated to an oil. To the oil dissolved in 2-propanol (125 ml) was added 75 ml of a saturated solution of etheral hydrogen chloride. The hydrochloride salt of the titled product crystallized slowly on standing at room temperature; wt. 18.8 g (76%), mp=211°–212°.

Analysis for: $C_{34}H_{33}F_2N_3O_2.HCl$: Calculated: C, 69.20; H, 5.81; Cl, 6.01; N, 7.12. Found: C, 69.20; H, 5.87; Cl, 6.11; N, 7.21.

EXAMPLE 9

1,2-Dibenzoylhexahydro-5H-1,2,5-triazepine-5-carboxylic acid 4,4-bis(4-fluorophenyl)ester A mixture of 4,4-bis(4-fluorophenyl)butyl bromide (24.4 g), 1,2-dibenzoyl-hexahydro-1H-1,2,5-triazepine hydrochloride (25.9 g) and powdered anhydrous potassium carbonate (52 g) in N,N-dimethylformamide (260 ml, dried over 4A molecular sieves) protected from moisture with a Drierite drying tube was stirred at room temperature for 48 hours. The mixture was filtered through sintered glass and the filtrate was evaporated under oil pump vacuum to an oil which was slurried in ether with silica as described in example 8. The resulting ethereal solution was evaporated to a thick syrup (45.2 g) which contained the titled product and 1,2-dibenzoyl-5-[4,4-bis(4-fluorophenyl)butyl]hexahydro-1H-1,2,5-triazepine as the major impurity. The syrup was dissolved in 2-propanol to bring the volume to approximately 120 ml. A similar volume of saturated ethereal hydrogen chloride was added to crystallize the crude hydrochloride of the impurity (5.8 g, mp=179°–184°). The mother liquor was concentrated and evaporated twice with benzene. Partitioning of the resulting syrup between benzene and 2N hydrochloric acid caused crystallization of a pure hydrate of the hydrochloride of 1,2-dibenzoyl-5-[4,4-bis(4-fluorophenyl)butyl]hexahydro-1H-1,2,5-triazepine from the benzene layer. The benzene layer was filtered and the crystals were washed with benzene; wt. 6.4 g (14%), mp=137°–141°.

Analysis for: $C_{34}H_{33}F_2N_3O_2.HCl.H_2O$: Calculated: C, 67.15; H, 5.97; Cl, 5.83; N, 6.91. Found: C, 67.45; H, 5.79; Cl, 6.00; N, 6.87.

Concentration of the benzene filtrate gave a further small crop of crystals, which were discarded. The benzene solution was washed with sodium carbonate solution and then with water until the washings were neutral. The dried (MgSO$_4$) solution was concentrated to a syrup which was chromatographed on a column of silica gel prepacked in dichloromethane. Elution with dichloromethane followed by dichloromethane ethyl acetate (9:1) allowed a separation of the titled product from minor impurities. The product was isolated as a foam (18.8 g, 42%).

Analysis for: $C_{35}H_{33}F_2N_3O_4$: Calculated: C, 70.34; H, 5.57; N, 6.36. Found: C, 69.76; H, 5.47; N, 7.11.

EXAMPLE 10

1,2-Dibenzoylhexahydro-5-[2-(4-pyridinyl)ethyl]-1H-1,2,5-triazepine

A mixture of 1,2-dibenzoyl-1H-1,2,5-triazepine (2.0 g), 4-vinylpyridine (1.42 g) and p-toluenesulfonic acid (1.21 g) in methanol (70 ml) was stirred and heated at 60° under a nitrogen atmosphere for 3 days. The foam, obtained after evaporation of the solvent, was mixed with dichloromethane and 10% sodium carbonate solution. The organic phase was washed with water until neutral washings were obtained and dried (Na$_2$SO$_4$). Evaporation of the solvent gave a foam, 2.25 g. The crude product was chromatographed on a column of silica gel; elution with ethanol-ethyl acetate-dichloromethane (1:4:5) giving a major component. A hydrochloride salt, ⅓ hydrate of the titled compound was formed in ethanol; wt. 1.2 g (38%), mp 247° dec.

Analysis for: $C_{25}H_{26}N_4O_2.2HCl.\frac{1}{3}H_2O$: Calculated: C, 60.85; H, 5.85; Cl, 14.37; N, 11.36; H$_2$O, 1.22. Found: C, 60.36; H, 5.63; Cl, 14.19; N, 11.27; H$_2$O, 1.22.

EXAMPLE 11

5-[4,4-Bis(4-fluorophenyl)butyl]hexahydro-1,2-bis(phenylmethyl)-1H-1,2,5-triazepine To lithium aluminum hydride (21 g) in ether (150 ml) was added 1,2-dibenzoyl-5-[4,4-bis(4-fluorophenyl)butyl]hexahydro-1H-1,2,5-triazepine hydrochloride (34.4 g) slowly in small portions. The mixture was stirred and heated under reflux with protection from moisture for 22 hours. The reaction was quenched with 10% sodium hydroxide and water. The resulting hydroxides were collected on a filter and washed well with ether. The filtrate and washings were evaporated to a syrup, wt. 30.4 g. The syrup was dissolved in acetone and the solution was decolorized (Nuchar). The solution was concentrated and a solution of fumaric acid (6.7 g) in acetone (800 ml) was added. The resulting solution was boiled down until crystallization occurred. After cooling, the crude product was collected on a filter and washed with acetone; wt. 32.9 g. Recrystallization from methanol-ether gave 25.3 g (68%) of pure titled product as the fumarate salt (1:1), mp=184°–185°.

Analysis for: $C_{34}H_{37}F_2N_3.C_4H_4O_4$: Calculated: C, 71.12; H, 6.44; N, 6.55. Found: C, 71.16; H, 6.40; N, 6.89.

EXAMPLE 12

5-[4,4-Bis(4-fluorophenyl)butyl]hexahydro-1H-1,2,5-triazepine

5-[4,4-bis(4-fluorophenyl)butyl]hexahydro-1,2-bis(phenylmethyl)-1H-1,2,5-triazepine fumarate (21.8 g) was stirred magnetically with ether and dilute sodium hydroxide solution until the solid had dissolved. The aqueous layer was separated and extracted twice more with ether. The combined ether extracts were washed with brine and dried (MgSO$_4$). Evaporation gave 18.3 g of the syrupy free base.

The free base (18.3 g), dissolved in ethanol (145 ml) and 2N hydrochloric acid (55 ml), was added to prehydrogenated 10% Palladium on carbon catalyst (3.5 g) suspended in ethanol (100 ml). The transfer was completed by the addition of a further 100 ml of ethanol. Hydrogenation of the mixture at atmospheric pressure and room temperature was allowed to proceed until the theoretical uptake had occurred. At this stage hydrogenation had essentially ceased. The catalyst was removed by filtration through Celite and washed well with ethanol. The filtrate and washings were evaporated to a gel which was subjected to an an oil pump vacuum overnight. The resulting solid was crushed to a powder and dried under oil pump vacuum over phosphorous pentoxide. The yield of titled product (dihydrochloride, 0.3 hydrate) as an amorphous powder was 13.8 g (96%).

Analysis for: $C_{20}H_{25}F_2N_3.2HCl.0.3H_2O$: Calculated: C, 56.69; H, 6.56; Cl, 16.73; N, 9.92; H$_2$O, 1.28. Found: C, 56.40; H, 6.63; Cl, 17.02; N, 9.82; H$_2$O, 0.94.

EXAMPLE 13

5-[4,4-Bis(4-fluorophenyl)butyl]hexahydro-1H-1,2,5-triazepine

A mixture of 1,2-dibenzoyl-5-[4,4-bis(4-fluorophenyl)butyl]hexahydro-1H-1,2,5-triazepine hydrochloride (30.4 g), n-butanol (230 ml), 12N hydrochloric acid (230 ml) and water (230 ml) was stirred and heated at 100° under reflux for 4 hours. The mixture was evaporated to an oil which was mixed with water (230 ml), ether and 12N hydrochloric acid (23 ml). After standing overnight a white solid was collected on a filter pad and washed with ether-water (1:1). The layered filtrate was separated and the aqueous layer diluted with water (300 ml). The solution was mixed with ethyl acetate and the mixture warmed to 35°. The aqueous layer was separated and it was extracted a further four times with ethyl acetate. The aqueous solution was evaporated to an oil which was subjected to an oil pump vacuum. Crude title compound, as the dihydrochloride, was obtained as a tan solid, 19.7 g (91%). This crude material was used in several of the examples cited.

EXAMPLE 14

1-Benzoyl-5-[4,4-bis(4-fluorophenyl)butyl]hexahydro-1H-1,2,5-triazepine

To a stirred solution of 5-[4,4-bis(4-fluorophenyl)butyl]hexahydro-1H-1,2,5-triazepine dihydrochloride (4.0 g, prepared as in example 13), N,N-diisopropylethylamine (8.36 ml) in dry dichloromethane (120 ml) at 5° under nitrogen was added a solution of benzyl chloride (1.11 ml) in dichloromethane (10 ml) and the solution was allowed to warm to room temperature while stirring for 4 hours. After extraction of the mixture with water, the dichloromethane solution was dried (Na$_2$SO$_4$) and evaporated to a solid. The crude product was chromatographed on a column of silica gel; elution with ethyl acetate-dichloromethane (1:1) giving a major component. A fumarate salt (1:1) of the titled compound was formed from this material in acetonitrile and was recrystallized from acetonitrile; wt. 1.8 g (33%), mp=135°–136°.

Analysis for: $C_{27}H_{29}F_2N_3O.C_4H_4O_4$: Calculated: C, 65.83; H, 5.88; N, 7.43. Found: C, 65.86; H, 6.05; N, 7.79.

EXAMPLE 15

5-[4,4-Bis(4-fluorophenyl)butyl]-N-ethylhexahydro-1H-1,2,5-triazepine-1-carboxamide To a stirred solution of 5-[4,4-bis(4-fluorophenyl)butyl]hexahydro-1H-1,2,5-triazepine dihydrochloride (3.25 g, prepared as in example 13), N,N-diisopropylethylamine (3.38 ml) in dry dichloromethane (10 ml) at 5° under nitrogen was added ethyl isocyanate (0.62 ml) in dichloromethane (10 ml) and the solution was stirred at room temperature overnight. After extraction of the mixture with water, the dichloromethane solution was dried (Na$_2$SO$_4$) and evaporated to an oil. The crude product was chromatographed on a column of silica gel prepacked in dichloromethane. Successive elution with ethyl acetate-dichloromethane (4:1) and ethanol-ethyl acetate-dichloromethane (1:4:5) allowed a separation of a major component from impurities. The hydrobromide salt of the titled compound was formed from the material in 2-propanol and was recrystallized from 2-propanol-ethyl acetate; wt. 2.18 g (49%), mp=130°–134° dec.

Analysis for: $C_{23}H_{30}F_2N_4O.2HBr$: Calculated: C, 47.76; H, 5.58; Br, 27.64; N, 9.69. Found: C, 47.78; H, 5.47; Br, 26.92; N, 9.58.

EXAMPLE 16

5-[4,4-Bis(4-fluorophenyl)butyl]-N,N'-diethyl-4,5,6,7-tetrahydro-1H-1,2,5-triazepine-1,2(3H)-dicarboxamide To a stirred mixture of 5-[4,4-bis(4-fluorophenyl)butyl]hexahydro-1H-1,2,5-triazepine dihydrochloride (8.0 g, prepared as in example 13), N,N-diisopropylethylamine (4.06 ml) in dry dichloroethane (60 ml) under nitrogen was added ethyl isocyanate (10.5 ml) in dichloromethane (15 ml) and the mixture heated at 55° (under reflux) for 3 days. After extraction of the mixture with a 10% sodium carbonate solution, the dichloroethane solution was dried (Na$_2$SO$_4$) was evaporated to a gum. The crude product was chromatographed on silica gel and a major component was eluted with ethanol-ethyl acetate-dichloromethane (1:4:5). A fumarate salt formed from this material in ethyl acetate and was recrystallized from ethyl acetate giving pure titled product as a 1:1 fumarate salt; wt. 3.97 g (34%), mp=171°–172°.

Analysis for: $C_{26}H_{35}F_2N_5O_2$: Calculated: C, 59.69; H, 6.51; N, 11.90. Found: C, 59.41; H, 6.53; N, 11.51.

EXAMPLE 17

5-[4,4-bis(4-fluorophenyl)butyl]hexahydro-N-phenyl-1H-1,2,5-triazepine-1-carboxamide To a stirred solution of 5-[4,4-bis(4-fluorophenyl)butyl]hexahydro-1H-1,2,5-triazepine dihydrochloride (4.5 g, prepared as in example 13) and triethylamine (5.92 ml) in dry dichloromethane (60 ml) at 5° under nitrogen was added phenyl isocyanate (1.19 ml) in dichloromethane (15 ml) and the solution was stirred at room temperature for 2 days. After extraction of the mixture with water, the dichloromethane solution was dried (Na$_2$SO$_4$) and evaporated to a gum. The crude product was chromatographed on a column of silica gel; a major component being eluted with ethanol—ethyl acetate—dichloromethane (1:4:5). A fumarate salt formed from this material in acetone and recrystallized from ethanol to give pure titled product as a 1:1 fumarate salt, wt. 2.60 g (42%), mp=187°-188° dec.

Analysis for: C$_{27}$H$_{30}$F$_2$N$_4$O.C$_4$H$_4$O$_4$: Calculated: C, 64.12; H, 5.90; N, 9.65. Found: C, 64.23; H, 5.87; N, 9.76.

EXAMPLE 18

5-[4,4-bis(4-fluorophenyl)butyl]-N-(2,6-dimethylphenyl)hexahydro-1H-1,2,5-triazepine-1-carboxamide To a stirred solution of 5-[4,4,-bis(4-fluorophenyl)butyl]hexahydro-1H-1,2,5-triazepine dihydrochloride (2.09 g, prepared as in example 12) in dry dichloromethane (15 ml) at 5° under nitrogen was added 2,6-dimethylphenyl isocyanate (0.7 ml) in dry dichloromethane (5 ml) dropwise. The solution was left at room temperature overnight. The resulting pale yellow solution was diluted with dichloromethane and washed consecutively with N sodium hydroxide and brine (×2). The dried (MgSO$_4$) extract was evaporated to an oil. The oil was dissolved in dichloromethane and the solution filtered through Celite. The filtrate was evaporated to an oil which gave 2.54 g of a white foam when subjected to an oil pump vacuum. A portion (2.48 g) of the foam was mixed with a solution of fumaric acid (0.585 g) in acetone (15 ml) and the mixture heated to boiling. Crystals of crude fumarate salt of the titled product was formed on cooling the clear solution; wt.=2.66 g (89%), mp=199°-201°. Recrystallization from ethanol-ether gave pure titled product as a 1:1 fumarate salt (2.42 g), mp=200°-202°.

Analysis for: C$_{29}$H$_{34}$F$_2$N$_4$O.C$_4$H$_4$O$_4$: Calculated: C, 65.12; H, 6.29; N, 9.20. Found: 65.46; H, 6.19; N, 9.39.

EXAMPLE 19

5-[4,4-Bis(4-fluorophenyl)butyl]-N-(2,6-dimethylphenyl)hexahydro-1H-1,2,5-triazepine-1-acetamide A mixture of 5-[4,4-bis(4-fluorophenyl)butyl]hexahydro-1H-1,2,5-triazepine dihydrochloride (1.82 g, prepared as in example 12), 2-chloro-N-(2,6-dimethylphenyl)acetamide (1.04 g), N,N-diisopropylethylamine (4.33 ml) and a catalytic quantity of potassium iodide in N,N-dimethylformamide (15 ml, dried over 4A molecular sieves) was heated at 110°-115° under nitrogen for 23 hours. The resulting dark solution was evaporated to a syrup under oil pump vacuum. The syrup was extracted with dichloromethane and the extract was washed consequtively with N sodium hydroxide (×2) and brine (×3). The dried (MgSO$_4$) extract was evaporated to a syrup which was subjected to an oil pump vacuum; wt. 2.17 g. The syrup was chromatographed on a column of silica gel prepacked in dichloromethane. Elution was wtih dichloromethane, dichloromethane ethyl acetate (4:1), ethyl acetate and finally dichloromethane-ethyl acetate-ethanol (5:4:1). The last mentioned solvent removed the product. Evaporation of appropriate fractions gave a syrup which was kept under nitrogen. Trituration with heptane afforded 1.35 g of a tan solid, mp=89°-91°. Crystallization from dichloromethane-heptane gave 1.21 g of the titled compound as the free base. A portion (1.20 g) of this material was converted into a dihydrobromide salt by treatment with ethereal hydrogen bromide. Recrystallization of this hygroscopic material from methanol-ether afforded 1.43 g (49%) of the titled product as a dihydrobromide, 0.3 hydrate having a mp=145°-148° (prior sintering).

Analysis for: C$_{30}$H$_{36}$F$_2$N$_4$O.2HBr.0.3H$_2$O: Calculated: C, 53.47; H, 5.77; Br, 23.72; N, 8.31; H$_2$O, 0.80. Found: C, 53.15; H, 5.47; Br, 24.21; N, 8.13; H$_2$O, 0.77.

EXAMPLE 20

Hexahydro-5-methyl-1,2-(phenylmethyl)-1H-1,2,5-triazepine 1,2-Dibenzoylhexahydro-5H-1,2,5-triazepine-5-carboxylic acid 4,4-bis(4-fluorophenyl)butyl ester (15.9 g, from example 9) in ether (250 ml) was added dropwise to stirred lithium aluminum hydride (8.5 g) in ether (700 ml). The mixture was stirred and heated unsder reflux ovenight. The reaction was quenched with 10% sodium hydroxide solution and the precipitated hydroxides collected on a filter. The filter cake was washed well with ether. The filtrate and washings were evaporated to a syrup which was subjected to an oil pump vacuum; wt. 15.0 g.

A similar reduction of another batch of starting material (5.9 g) gave 5.4 g of the above mentioned syrupy material. The two batches (15.0 g and 5.4 g) were dissolved in ether and combined. The ether solution was extracted with dilute hydrochloric acid. After a further two extractions with ether, the aqueous solution was made alkaline by the addition of sodium hydroxide solution. Extraction (×3) with ether gave a solution enriched in the free base of the titled product. The dried (Na$_2$SO$_4$) extracts were evaporated to an oil. A hydrochloride of this material (the titled compound), was formed in ethanol-ether; wt. 11.2 g (84%), mp=231°-232° dec.

Analysis for: C$_{19}$H$_{25}$N$_3$.2HCl: Calculated: C, 61.95; H, 7.39; N, 11.41; Cl, 19.25. Found: C, 61.87; H, 7.30; N, 11.43; Cl, 19.18.

EXAMPLE 21

Hexahydro-5-methyl-1H-1,2,5-triazepine

A mixture of hexahydro-5-methyl-1,2-(phenylmethyl)-1H-1,2,5-triazepine dihydrochloride (8.0 g), 10% palladium on carbon (0.8 g), N hydrochloric acid (50 ml) in ethanol (50 ml) was hydrogenated at atmospheric pressure at room temperature until uptake ceased. The catalyst was collected on a filter and washed with water. The filtrate and washings were evaporated and the residue was crystallized from ethanol; wt. of titled product (as a dihydrochloride salt), 4.0 g, (97%), mp=150°-151° dec.

Analysis for: C$_5$H$_{13}$N$_3$.2HCl: Calculated: C, 31.92; H, 8.04; N, 22.34; Cl, 37.70. Found: C, 31.43; H, 7.87; N, 22.00; Cl, 37.20.

EXAMPLE 22

N-(2,6-dimethylphenyl)hexahydro-5-methyl-1H-1,2,5-triazepine-1-carboxamide

To a stirred solution of hexahydro-5-methyl-1H-1,2,5-triazepine dihydrochloride (3.7 g), N,N-diisopropylethylamine (10.25 ml) in dry dichloromethane (20 ml) under nitrogen was added 2,6-dimethylphenyl isocyanate (3.01 ml) in dry dichloromethane (10 ml) slowly dropwise. The solution was stirred under nitrogen at room temperature overnight. After extraction of the reaction mixture with water, the dichloromethane solution was dried (Na$_2$SO$_4$) and evaporated to a solid. The crude free base of the titled product was recrystallized from benzene-hexane (wt. 3.2 g) and then from ethyl acetate (wt. 2.15 g).

A fumarate salt of the titled product formed from this material in 2-propanol and was recrystallized from ethanol; wt. 2.4 g (32%), mp=176°-177° dec.

Analysis for: $C_{14}H_{22}N_4O \cdot C_4H_4O_4$: Calculated: C, 57.12; H, 6.93; N, 14.81. Found: C, 56.91; H, 6.98; N, 14.74.

What is claimed is:

1. A compound of the formula

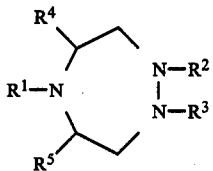

I or a pharmaceutically acceptable acid addition salt thereof, wherein $R^4$ and $R^5$ are independently hydrogen or $C_1$–$C_4$ alkyl;

$R^1$ is $(R^6)_2$—CH—$(CH_2)_n$— in which n is 0, 1, 2 or 3 and $R^6$ is p-fluoro, chloro or methoxyphenyl; and $R^3$ is hydrogen and $R^2$ is benzoyl, 2,6-dimethyl or diethylbenzoyl, 2,6-dichlorobenzoyl, N-methyl, ethyl or propylcarboxamido, N-phenylcarboxamido, N-2,6-dimethyl or diethylphenylcarboxamido, N-2,6-dichlorophenylcarboxamido, N-methyl, ethyl or propylacetamido, N-phenylacetamido, N-2,6-dimethyl or diethylphenyl-acetamido, or N-2,6-dichlorophenylacetamido; or $R^2$ and $R^3$ are the same and are N-methyl, ethyl or propylcarboxamido, benzoyl, 2,6-dimethyl or diethylbenzoyl, 2,6-dichlorobenzoyl, benzyl, 2,6-dimethyl or diethylbenzyl, 2,6-dichlorobenzoyl, or a removable amino protective group.

2. A compound of claim 1 in which $R^4$ and $R^5$ are independently hydrogen or methyl.

3. A compound of claim 1 in which $R^4$ and $R^5$ are hydrogen.

4. A compound of claim 1 in which n in $R^1$ is 3.

5. A compound of claim 1 in which $R^6$ in $R^1$ is p-fluorophenyl.

6. A compound of claim 1 in which $R^3$ is hydrogen and $R^2$ is N-methylcarboxamido, N-ethylcarboxamido, 2,6-dimethylbenzyl, N-phenylcarboxamide, N-2,6-dimethylphenylcarboxamido, N-methylacetamido, N-phenylacetamido, or N-2,6-dimethylphenylacetamido.

7. A compound of claim 1 in which $R^3$ is hydrogen and $R^2$ is N-phenylcarboxamido, N-2,6-dimethylphenylcarboxamido, benzoyl or N-2,6-dimethylphenylacetamido.

8. A compound of claim 1 in which $R^2$ and $R^3$ are the same and are benzoyl or benzyl.

9. A compound of claim 1 in which the removable amino protective group comprising $R^2$ and $R^3$ is selected from a group comprising $C_1$–$C_6$ alkanoyl, halo or dihalo ($C_1$–$C_6$)alkanoyl, pyridinoyl, t-butyloxycarbonyl, trichloroacetyl, $C_1$–$C_6$ alkoxycarbonyl and p-methoxybenzyl.

10. A compound of claim 1 selected from the group comprising 1,2-dibenzoyl-5-[4,4-bis(4-fluorophenyl)-butyl]-hexahydro-1H-1,2,5-triazepine and 5-[4,4-bis(4-fluorophenyl)butyl]-hexahydro-1,2-bis(phenylmethyl)-1H-1,2,5-triazepine.

11. A compound of claim 1 which is 5-[4,4-bis(4-fluorophenyl)butyl]-N-ethylhexahydro-1H-1,2,5-triazepine-1-carboxamido or a pharmaceutically acceptable acid addition salt thereof.

12. A compound of claim 1 which is 5-[4,4-bis(4-fluorophenyl)butyl]-N,N'-diethyl-4,5,6,7-tetrahydro-1H-1,2,5-triazepine-1,2(3H)-dicarboxamido or a pharmaceutically acceptable acid addition salt thereof.

13. A compound of claim 1 which is 5-[4,4-bis(4-fluorophenyl)butyl]-hexahydro-N-phenyl-1H-1,2,5-triazepine-1-carboxamido or a pharmaceutically acceptable acid addition salt thereof.

14. A compound of claim 1 which is 5-[4,4-bis(4-fluorophenyl)butyl]-N-(2,6-dimethylphenyl)hexahydro-1H-1,2,5-triazepine-1-carboxamide or a pharmaceutically acceptable acid addition salt thereof.

15. A compound of claim 1 which is 1-benzoyl-5-[4,4-bis(4-fluorophenyl)butyl]hexahydro-1H-1,2,5-triazepine or a pharmaceutically acceptable acid addition salt thereof.

16. A compound of claim 1 which is 5-[4,4-bis(4-fluorophenyl)butyl]-N-2,6-(dimethylphenyl)hexahydro-1H-1,2,5-triazepine-1-acetamido or a pharmaceutically acceptable acid addition salt thereof.

17. A compound of the formula

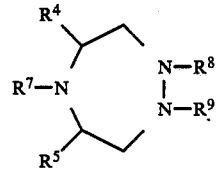

II or a pharmaceutically acceptable acid addition salt thereof, wherein $R^4$ and $R^5$ are independently hydrogen or $C_1$–$C_4$ alkyl;

$R^7$ is $C_1$–$C_4$ alkyl; and $R^9$ is hydrogen and $R^8$ is N-2,6-dimethyl, diethyl or dichlorophenylcarboxamido or N-2,6-dimethyl, diethyl or dichlorophenylacetamido.

18. A compound of claim 17 in which $R^4$ and $R^5$ are hydrogen or methyl.

19. A compound of claim 17 in which $R^5$ and $R^5$ are hydrogen.

20. A compound of claim 17 in which $R^7$ is methyl or ethyl.

21. A compound of claim 17 in which $R^9$ is hydrogen and $R^8$ is N-2,6-dimethyl or diethylphenylcarboxamido.

22. A compound of claim 17 which is N-(2,6-dimethylphenyl)hexahydro-5-methyl-1H-1,2,5-triazepine-1-carboxamide.

23. A compound of claim 17 which is N-(2,6-dimethylphenyl)hexahydro-5-ethyl-1H-1,2,5-triazepine-1-carboxamide.

* * * * *